US010458045B2

(12) United States Patent
Lim et al.

(10) Patent No.: US 10,458,045 B2
(45) Date of Patent: *Oct. 29, 2019

(54) BRUSH WITH MAGNETIC FILAMENTS

(71) Applicant: HCT ASIA LTD., Central (CN)

(72) Inventors: Sean Yuei (Cindy) Lim, Santa Monica, CA (US); Jin Chul Kim, Santa Monica, CA (US)

(73) Assignee: HCT ASIA LTD., Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,957

(22) Filed: Jul. 11, 2017

(65) Prior Publication Data

US 2017/0314164 A1    Nov. 2, 2017

Related U.S. Application Data

(63) Continuation of application No. 13/209,187, filed on Aug. 12, 2011, now Pat. No. 9,725,828.

(30) Foreign Application Priority Data

Nov. 5, 2010   (CN) .......................... 2010 1 0539244
Jan. 25, 2011   (CN) .......................... 2011 1 0029842

(51) Int. Cl.
| | |
|---|---|
| *A61N 2/00* | (2006.01) |
| *A46B 9/02* | (2006.01) |
| *A46B 15/00* | (2006.01) |
| *A46D 1/00* | (2006.01) |
| *D01F 6/62* | (2006.01) |
| *D01F 1/10* | (2006.01) |

(52) U.S. Cl.
CPC ................ *D01F 6/62* (2013.01); *A46B 9/021* (2013.01); *A46B 15/0026* (2013.01); *A46D 1/0207* (2013.01); *A61N 2/00* (2013.01); *D01F 1/10* (2013.01)

(58) Field of Classification Search
CPC .. A46D 1/0207; A46B 15/0026; A46B 9/021; A61N 2/00–12
See application file for complete search history.

(56) References Cited

U.S. PATENT DOCUMENTS

| | | |
|---|---|---|
| 1,831,393 A | 11/1931 | Pierce, Jr. |
| 3,867,299 A | 2/1975 | Rohatgi |
| 4,381,159 A | 4/1983 | Payne |

(Continued)

FOREIGN PATENT DOCUMENTS

| | | |
|---|---|---|
| CN | 2120557 U | 11/1992 |
| CN | 1199590 A | 11/1998 |

(Continued)

OTHER PUBLICATIONS

Beautyencounter, "iTech Magnetic & Tourmaline Boar and Nylon Bristle Brush 3 1/4 Inch," at http://www.beautyencounter.com/727428765006.html 1 page, retrieved on Sep. 7, 2010.

*Primary Examiner* — Thaddeus B Cox
(74) *Attorney, Agent, or Firm* — Seager, Tufte & Wickhem LLP

(57) ABSTRACT

A brush with magnetic filaments is described. The brush may be used, for example, as a brush for applying a cosmetic material. The filaments of the brush may, in one example, be made of a synthetic material infused with magnetic material.

11 Claims, 6 Drawing Sheets

(56) References Cited

U.S. PATENT DOCUMENTS

| | | | |
|---|---|---|---|
| 4,502,497 A | 3/1985 | Siahou | |
| 6,342,167 B1 | 1/2002 | Kawano et al. | |
| 7,159,950 B2 | 1/2007 | Young-Chul | |
| 7,530,752 B2 | 5/2009 | Gueret | |
| 7,918,620 B2 | 4/2011 | Del Ponte | |
| 8,060,971 B1 | 11/2011 | Castelluccio | |
| 8,074,666 B2 | 12/2011 | Piao | |
| 8,132,285 B2 | 3/2012 | Piao | |
| 8,185,998 B2 | 5/2012 | Xu | |
| 2001/0003600 A1 | 6/2001 | Guay | |
| 2001/0006069 A1* | 7/2001 | Treskov | B26B 21/40 132/290 |
| 2002/0164192 A1 | 11/2002 | Gueret | |
| 2002/0182409 A1 | 12/2002 | Gueret | |
| 2005/0011030 A1 | 1/2005 | Gonzalez | |
| 2006/0174436 A1 | 8/2006 | Brezler | |
| 2009/0039995 A1 | 2/2009 | Kipp et al. | |

FOREIGN PATENT DOCUMENTS

| | | |
|---|---|---|
| CN | 1308500 A | 8/2001 |
| DE | 3905043 A1 | 8/1990 |
| JP | 2006271983 A | 10/2006 |

\* cited by examiner

BRUSH WITH MAGNETIC FILAMENTS

RELATED APPLICATIONS

This application is a continuation application of U.S. patent application Ser. No. 13/209,187, filed on Aug. 12, 2011, now U.S. Pat. No. 9,725,828, which claims priority to Chinese Patent Application Serial No. 201110029842.6, filed on Jan. 25, 2011, and Chinese Patent Application Serial No. 201010539244.9, filed on Nov. 5, 2010, which are incorporated by reference herein in their entireties.

BACKGROUND

Many cultures, including those in Egypt, China, Persia, and Europe, used magnets in one form or another to treat ailments, disorders and wounds. The basic theory behind magnetic therapy is that the force of the positively charged particles is able to influence the molecules in the body without touching them.

Magnetic therapy continues to be practiced by a large segment of the population today. As noted above, magnetic therapy treatment is typically used to treat ailments and not as part of a daily routine.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Overview

Figure 1:
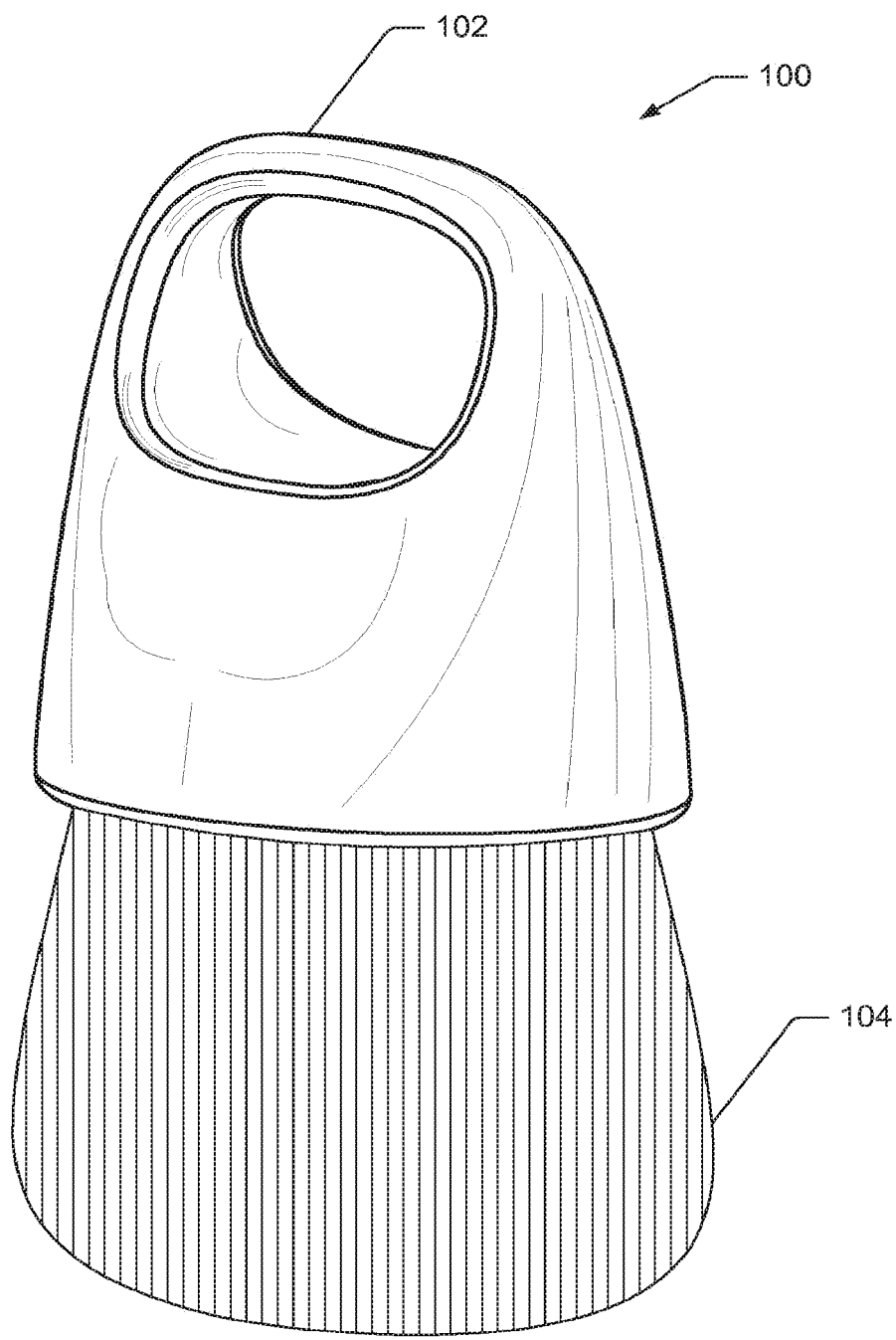
FIG. 1 is a schematic diagram of an example brush having magnetic filaments including a permanent magnetic material.

As noted above, magnetic therapy treatment is typically used to treat ailments and not as part of a daily routine. This disclosure describes a brush having magnetic filaments or fibers that can be used, not only for magnetic therapy, but also as part of a user's daily routine. Throughout the application, embodiments are described in terms of brushes having filaments. However, in some embodiments, brushes may be formed using other types of natural and/or synthetic fibers. The term "fiber" is used herein to encompass synthetic magnetic filaments and other types of natural and/or synthetic fibers. The brush may be used, for example, to apply a cosmetic material. The brush may, but need not, be used in connection with a cosmetic product containing magnetic particles (e.g., magnetized minerals that are incorporated into product as an ingredient). While the application describes the fibers for use in a cosmetic brush, magnetic fibers according to this application are usable in other applications such as, for example, mascara brush, toothbrushes, hair brushes, etc.

The application further describes methods and processes for manufacturing magnetic filaments usable to make brushes and other products employing filaments.

The magnetic fibers provide a static or permanent magnet, which is thought to aid in circulation, while the magnetized particles in the cosmetic product (if used) are thought to help remove toxins, decrease inflammation, and reactivate procollagen synthesis to add back elasticity and suppleness in mature skin.

Thus, by using the brush with magnetic fibers described herein, users are able to achieve the benefits of magnetic therapy as part of their daily routine. Moreover, users needn't even buy products with magnetized ingredients to receive benefits of magnetic therapy. Rather, users may simply use the magnetic brush with the skincare or cosmetic products they already have to get the results of magnetic therapy.

Generally, brushes according to this application include magnetic fibers. The fibers may comprise synthetic filaments or natural fibers. The fibers may be coated with a magnetic material and, in the case of synthetic filaments, may additionally or alternatively be infused or impregnated with magnetic material.

Examples of natural fibers that could be used include, without limitation, any supple fibers such as hair, cellulose fibers, cotton, hemp, flax, or the like.

Examples of synthetic materials that may be used to form the filaments include, without limitation, taklon, nylon, Polybutylene Terephthalate (PBT), Polyethylene Terephthalate (PET), polyester and/or Polypropylene (PP).

Examples of magnetic materials that may be used include permanent magnetic materials such as strontium ferrite, barium ferrite, magnetite and/or hematite. The magnetic materials may be in powder form or granular form, for example. The magnetic materials may be applied to the fibers using an adhesive or bonding process and/or, in the case of synthetic materials, may be added to the synthetic resin prior to extrusion, sintering, or other forming process.

In another example, the brush may comprise fibers including a ferrous, copper, or other conductive material, and the magnetic character of the fibers may be imparted, at least in part, by an electromagnet or a permanent magnet housed in a ferrule and/or handle of the brush and configured to induce a magnetic field in the fibers of the brush. In such an example, the ferrule and/or handle of the brush may be at least partially formed of a ferromagnetic material capable of transferring electricity and/or magnetism from the electromagnet and/or permanent magnet to the fibers of the brush. In some examples the fibers may be magnetized by being coated and/or infused with a magnetic material, as well as by an electromagnet or permanent magnet in the ferrule or handle of the brush.

By way of example, synthetic filaments used for magnetic fibers may include greater than or equal to 80%, but less than 100%, of synthetic materials such as PBT resin and/or PET resin, and less than or equal to 20% of magnetic or conductive materials. As noted above, the magnetic materials may include strontium ferrite, barium ferrite, magnetite and/or hematite. In one example, synthetic filaments may include between about 5% and about 15% of strontium ferrite. In one specific example, the synthetic filaments may include about 5% strontium ferrite. The amount of strontium ferrite or other magnetic material may be varied based on the desired strength of magnetic field to be generated by the filament. All of the foregoing percentages are by weight of material.

In one example, magnetic fibers of a brush may have a diameter of between about 0.05 mm and about 0.25 mm. In some examples, magnetic fibers of a cosmetic brush may have a diameter of between about 0.05 mm and about 0.075 mm. However, in other examples, fibers may have other greater or smaller diameters.

In still other examples, a sponge, foam, flocking, or other type of applicator may be coated and/or infused with magnetic material, rather than a brush.

The magnetic material may be coated or infused in natural or synthetic fibers, or other types of applicators using a variety of techniques. For example, in the case of synthetic fibers, the synthetic fibers may be formed using a magnetic resin mixture including both synthetic resin and magnetic material. In other examples, natural fibers, synthetic fibers, and/or other applicators may be coated or infused with magnetic materials by dipping the applicator in a liquid solution containing the magnetic material, soaking the applicator in a solution containing the magnetic material, spraying the magnetic material onto the applicator, applying the magnetic material to the applicator using a vapor deposition process, or the like. In still other examples, the magnetic material may be adhered to the applicator using an adhesive or binder.

Example Embodiments

FIG. 1 is a schematic diagram of an example brush 100 having a handle 102 and magnetic fibers 104 including a permanent magnetic material, such as those described above. As noted above, the magnetic material may be coated on and/or impregnated in the fibers of the brush.

Figure 2:
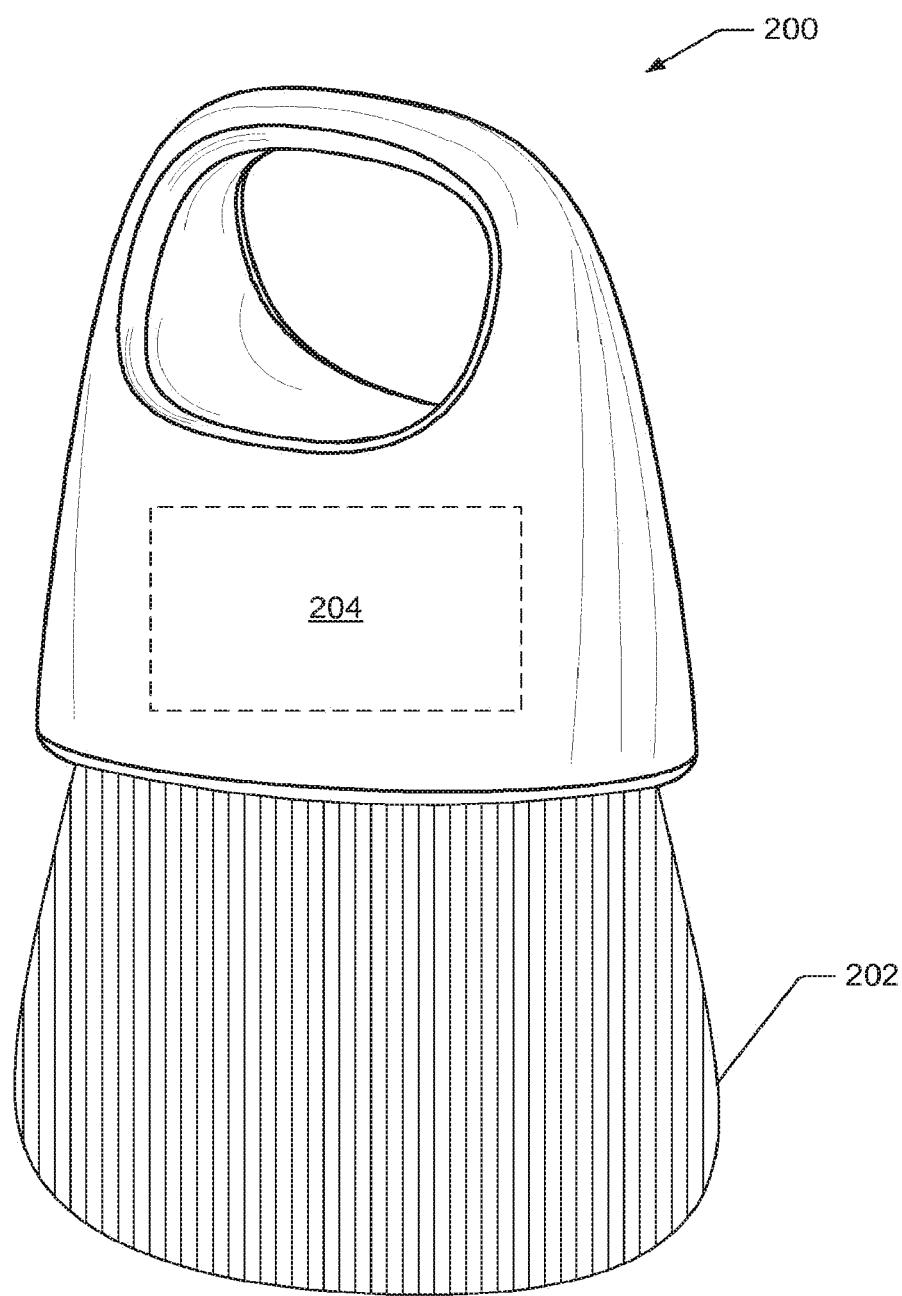
FIG. 2 is a schematic diagram of another example brush having magnetic filaments that are magnetized at least in part by an electromagnet.

FIG. 2 is a schematic diagram of another example brush 200 having magnetic fibers 202 that are magnetized at least in part by an electromagnet 204 disposed in a handle, ferrule, or other portion of the brush 200. In this example, the fibers are coated with and/or impregnated/infused with a conductive material, such as those described above. Additionally or alternatively, the brush 200 may include a permanent magnet or ferromagnetic plate 206 disposed in the handle, ferrule, or other portion of the brush. In some embodiments, the plate 206 may be disk shaped and may be coupled to the electromagnet (if provided). In one specific example, the plate 206 may comprise a metal plate to distribute magnetic flux evenly from the electromagnet. In an alternative specific example, the plate 206 may comprise a permanent magnet, a magnetized metal plate, or a magnetized synthetic plate made of a synthetic material such as any of those described herein for the manufacture of the magnetic filaments and may be arranged to apply magnetic flux evenly from the plate 206 to the fibers 202. Thus, the plate 206 may enhance or supplement a magnetic charge of the fibers 202.

Figure 3:
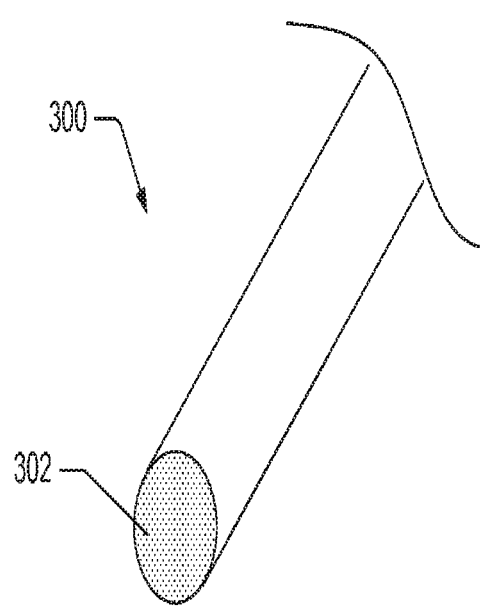
FIG. 3 is a partial cross-sectional view of an example filament infused with magnetic material.

FIG. 3 is a partial cross-sectional view of an example fiber 300 infused with magnetic material 302. In this example, the fiber 300 is shown as a synthetic filament, which may be infused with magnetic material 302 according to the example process described with reference to FIG. 5 below.

Figure 4:
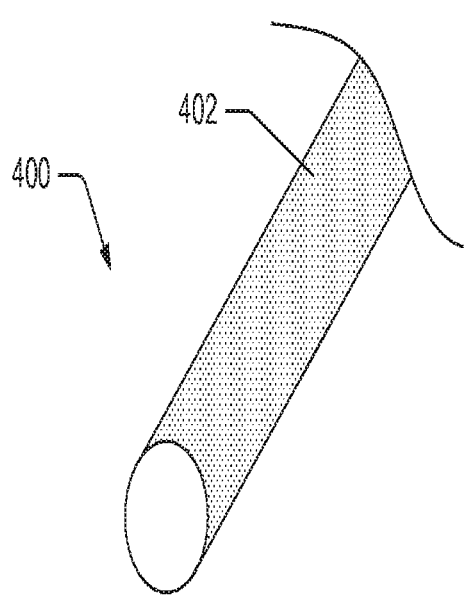
FIG. 4 is a partial cross-sectional view of an example filament coated with magnetic material.

FIG. 4 is a partial cross-sectional view of an example fiber 400 coated with magnetic material 402. In this example, the fiber 400 is shown as a natural fiber, which may be coated or infused with the magnetic material by, for example, applying an adhesive or binder to the fiber, applying a magnetic material to the coated fiber, and curing the adhesive or binder to hold the magnetic material in place. However, as discussed above, in other examples, fibers and other applicators may be coated and/or impregnated with magnetic materials using other processes as well.

Figure 5:
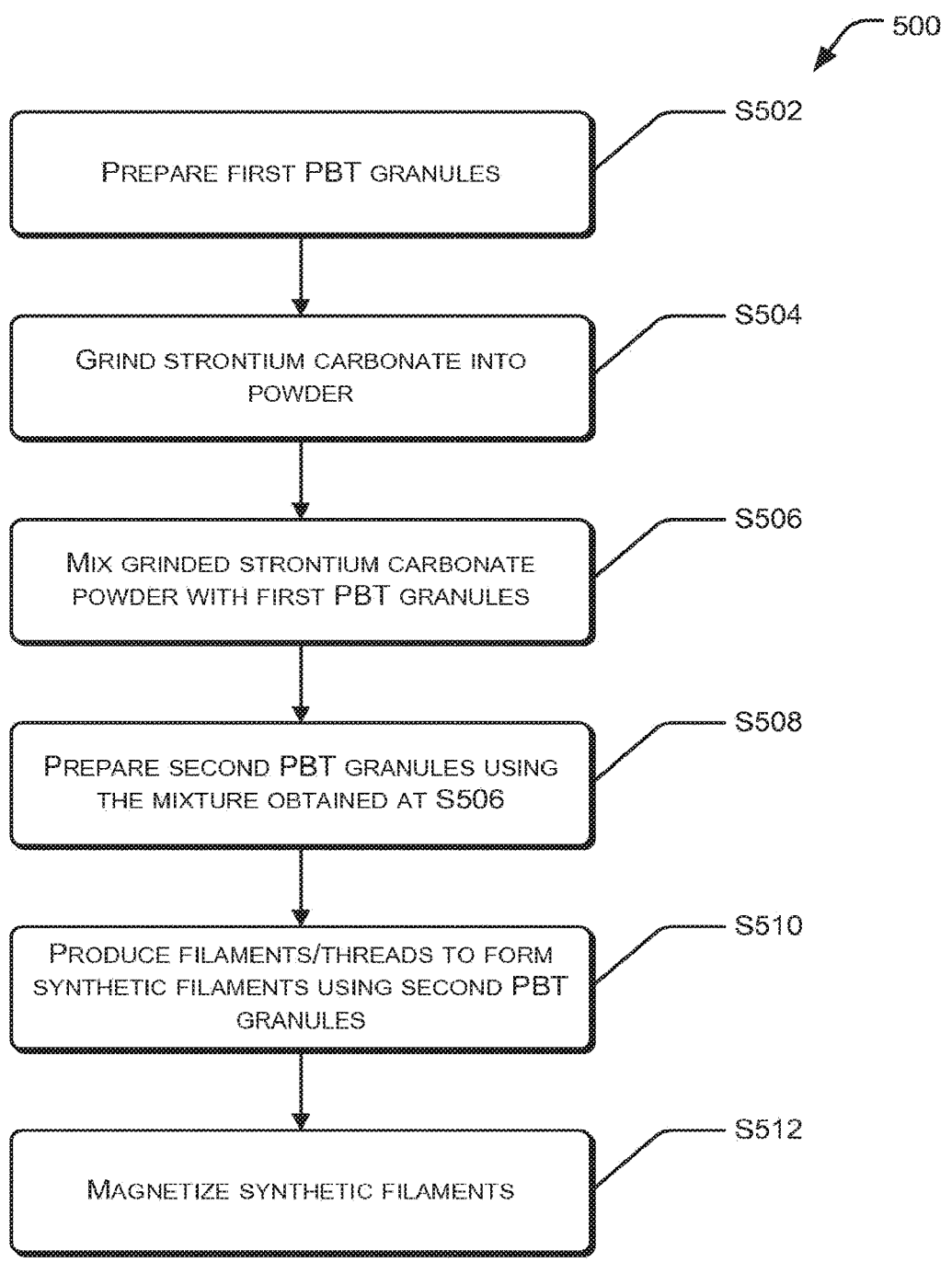
FIG. 5 is an example process of preparing magnetic synthetic filaments.

FIG. 5 is an example process 500 of preparing a magnetic synthetic filament. At block S502, synthetic material such as PBT granules are prepared (hereinafter, "PBT granules"). These PBT granules may include nylon or other synthetic materials. Further, in other examples, other synthetic resins may be used, such as those described above. At block S504, magnetic material or conductive material such as strontium ferrite is ground into powder or granules. A grinding machine having a granularity of, for example, 800 micrometers or more may be used to grind the strontium ferrite or other magnetic material. At block S506, ground strontium ferrite (e.g., 20% by weight of strontium ferrite) or other magnetic material is evenly mixed with the prepared PBT granules to produce a magnetic resin mixture.

The amount of strontium ferrite may be varied, and can be adjusted accordingly based on the desired magnitude of magnetic strength. In one example, the amount of strontium ferrite may be less than or equal to 20%. Optionally, at block S508, the magnetic resin mixture may be adjusted by adding additional strontium ferrite powder (block S510) to form a magnetic resin mixture having higher strontium ferrite content and/or by adding additional resin (block S512) to obtain a magnetic resin mixture having higher resin content. Generally, higher relative strontium ferrite powder content will increase the magnetic character of the filaments. Conversely, higher relative resin content will produce filaments having increased elasticity and suppleness.

At block S514, magnetic resin mixture may be used to produce magnetic synthetic filaments. The synthetic filaments may be formed, for example, by extrusion. In one aspect, magnetic synthetic filaments produced using merely the magnetic resin mixture prepared at block S506 may be relatively rigid, whereas filaments prepared with a magnetic resin mixture prepared according to block S512 tend to be relatively elastomeric and supple.

Upon forming the synthetic filaments through the above blocks, the synthetic filaments may be stimulated (e.g., by applying a magnetic field to the filaments) in order to magnetize the synthetic filaments at block S516. The strength of the magnetic field and the duration of exposure to the magnetic field will determine the magnitude of magnetic charge imparted to the synthetic filaments. In one example, the filaments may be exposed to a magnetic field having a field strength of about 5 to about 10 Gauss. In one embodiment, the filaments may be exposed to the magnetic field for about 3 seconds. The length of exposure of the filaments to a magnetic field may be increased or decreased depending on, for example, an amount of magnetic material in the filament, a diameter of the filament, and/or a desired magnetic character of the filaments.

As discussed above, the proportions of the materials for producing the synthetic filaments may be adjusted differently to achieve different elasticity and suppleness of the filaments. The rigidity or stiffness of the filaments may also be adjusted by varying the proportions of the materials. Thus, significant control may be placed on the degree of suppleness and the magnitude of magnetic strength of the filaments.

In one example, the synthetic filaments produced according to the above process include PBT resin and strontium ferrite in amounts within the ranges for those materials set forth above.

Figure 6:
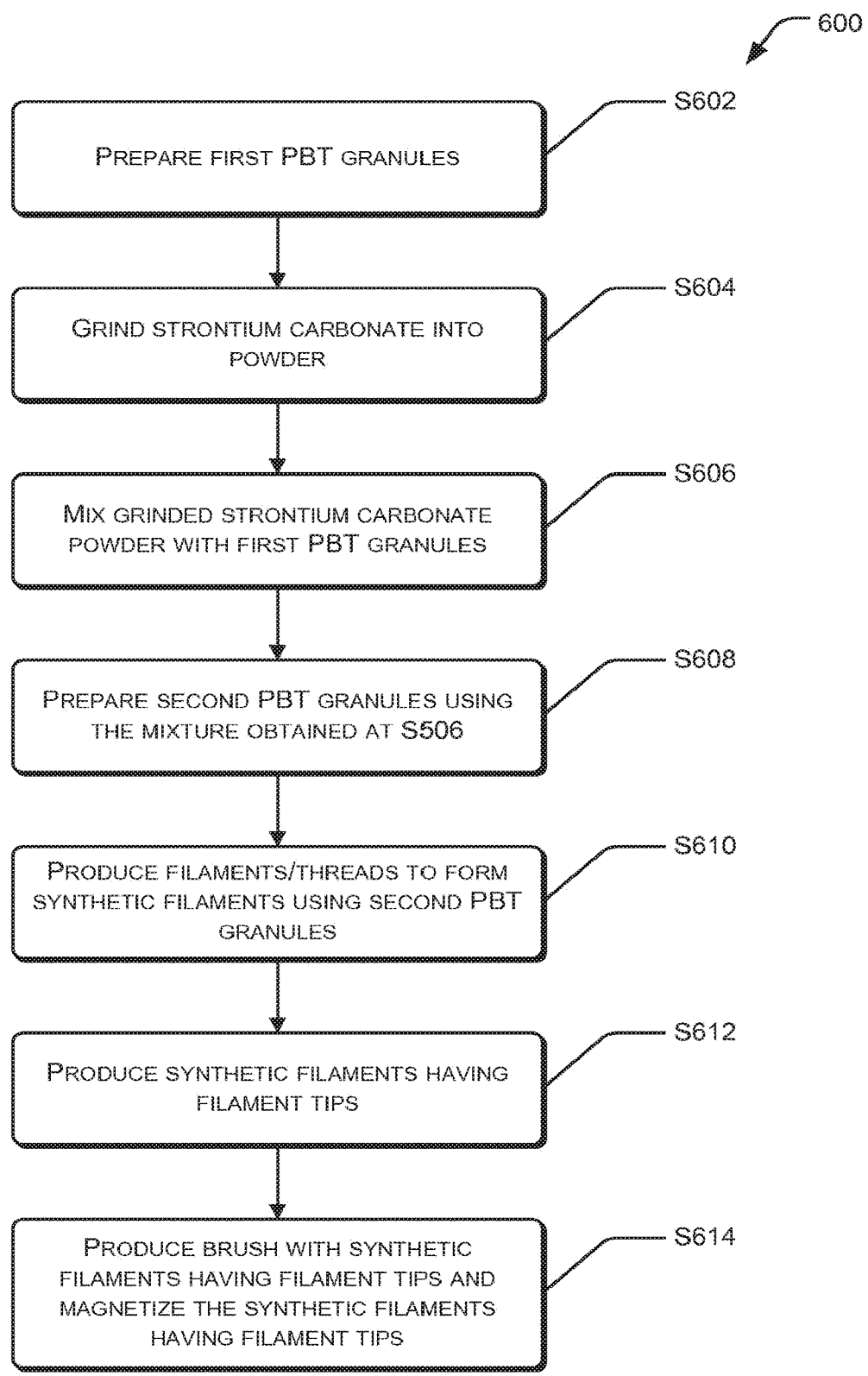
FIG. 6 is an example process of preparing a magnetic brush having magnetic filaments.

FIG. 6 is an example process 600 of preparing a magnetic brush using magnetic fibers, such as the synthetic filaments made by the process 500. As shown in FIG. 6, at block S602, filament tipping may be preformed on filaments formed according to block S514 or S516 according to conventional "filament tipping" techniques to produce synthetic filaments having suitable filament tips.

At block S604, a brush, such as brush 100 or 200, is produced by coupling the synthetic filaments having the tips to a brush handle. The filaments may be coupled to the handle by, for example, a ferrule. If the filaments are not magnetized prior to coupling to the brush, they may be stimulated, at S606, by applying a magnetic field to the synthetic filaments in order to cause filaments of the brush to possess a magnetic character. As a result, a magnetic brush is produced.

The synthetic filaments and brushes of the present disclosure have magnetic character. When used, blood circulation of a human body may be promoted due to its magnetic character. The effects of the brush may be further enhanced by inclusion of a permanent magnet or an electromagnet in a ferrule or handle of the brush.

CONCLUSION

Although the disclosure uses language specific to structural features and/or methodological acts, the embodiments are not limited to the specific features or acts described. Rather, the specific features and acts are disclosed as illustrative forms of implementing the embodiments.

Furthermore, the order in which the methods are described is not intended to be construed as a limitation, and any number of the described method blocks can be combined in any order to implement the methods, or alternate methods. Additionally, individual blocks may be deleted from the methods without departing from the spirit and scope of the subject matter described herein.

What is claimed is:

1. A cosmetic brush for simultaneously applying a skin-care product and magnetic therapy comprising:
    an elongate handle having first and second ends and a longitudinal axis extending therebetween;
    a cosmetic applicator coupled to the first end of the handle and extending substantially parallel to the longitudinal axis, the cosmetic applicator comprising a plurality of supple natural fibers infused with a permanently magnetic material; and
    a magnet disposed in the handle;
    wherein the cosmetic applicator has a magnetic character comprising first and second magnetic fields, wherein the second magnetic field supplements the first magnetic field.

2. The cosmetic brush of claim 1, wherein the first magnetic field is provided by the permanently magnetic material, and the second magnetic field is provided by the magnet.

3. The cosmetic brush of claim 1, wherein the magnet distributes a magnetic flux into the plurality of fibers.

4. The cosmetic brush of claim 3, further comprising a magnetic plate disposed between the magnet and the plurality of supple natural or synthetic fibers to evenly distribute the magnetic flux of the magnet into the plurality of supple natural or synthetic fibers.

5. The cosmetic brush of claim 1, wherein the supple natural fibers comprise hair, cellulose fibers, cotton, hemp or flax.

6. The cosmetic brush of claim 1, wherein the magnet comprises an electromagnet.

7. The cosmetic brush of claim 1, wherein the permanently magnetic material comprises magnetic granules.

8. The cosmetic brush of claim 1, wherein the natural fibers are infused by soaking the natural fibers in a solution containing the magnetic material.

9. The cosmetic brush of claim 8, wherein the natural fibers consist of one or more of hair, hemp, or flax.

10. A cosmetic brush for simultaneously applying a skin-care product and magnetic therapy comprising:
    an elongate handle having first and second ends and a longitudinal axis extending therebetween;
    a cosmetic applicator coupled to the first end of the handle and extending substantially parallel to the longitudinal axis, the cosmetic applicator comprising a plurality of supple natural fibers coated in or infused with a permanently magnetic material; and
    a magnet disposed in the handle;
    wherein the cosmetic applicator has a magnetic character comprising first and second magnetic fields, wherein the second magnetic field supplements the first magnetic field;
    wherein the permanently magnetic material comprises strontium ferrite, magnetite, and/or hematite.

11. A cosmetic brush for simultaneously applying a skin-care product and magnetic therapy comprising:
    an elongate handle having first and second ends and a longitudinal axis extending therebetween;
    a cosmetic applicator coupled to the first end of the handle and extending substantially parallel to the longitudinal axis, the cosmetic applicator comprising a plurality of supple natural fibers coated in or infused with a permanently magnetic material; and
    a magnet disposed in the handle;
    wherein the cosmetic applicator has a magnetic character comprising first and second magnetic fields, wherein the second magnetic field supplements the first magnetic field;
    wherein the permanently magnetic material comprises magnetic powder.

* * * * *